United States Patent [19]

Maliga

[11] Patent Number: 4,501,558
[45] Date of Patent: Feb. 26, 1985

[54] ULTRASONIC DENTAL CLEANING TIP STABILIZER

[76] Inventor: Joachim H. Maliga, 4014 8th Ave., Brooklyn, N.Y. 11232

[21] Appl. No.: 589,674

[22] Filed: Mar. 15, 1984

[51] Int. Cl.³ .............................................. A61C 1/07
[52] U.S. Cl. ..................................................... 433/86
[58] Field of Search .................................. 433/86, 119

[56] References Cited

U.S. PATENT DOCUMENTS

| | | | |
|---|---|---|---|
| 3,124,878 | 3/1964 | Bodine, Jr. et al. | 433/119 |
| 3,526,036 | 9/1970 | Goof | 433/119 |

Primary Examiner—Robert Peshock
Attorney, Agent, or Firm—McAulay, Fields, Fisher, Goldstein & Nissen

[57] ABSTRACT

In an ultrasonic dental cleaning and scaling device, the ultrasonically energized scaling tip and the water nozzle are positioned adjacent to one another. The scaling tip is within a grooved shield and the water nozzle is positioned along the longitudinal groove of the shield. A wafer like stabilizing element is positioned and mounted around the shield. A tab portion of the stabilizer extends into the groove of the shield to fix the rotational position of the stabilizer. A small opening in the tab portion of the stabilizer accepts the water nozzle thereby positioning the water nozzle relative to the scaling tip and the shield.

4 Claims, 5 Drawing Figures

ULTRASONIC DENTAL CLEANING TIP STABILIZER

BACKGROUND OF THE INVENTION

The present invention relates to a stabilizer for an ultrasonic dental cleaning tip and more paticularly to a stabilizer which prevents undesired motion of the water nozzle of the ultrasonic cleaning device.

Ultrasonic dental cleaning devices which have both a scaling tip and a water nozzle in close proximity to one another are well known in the art. These tips are used to clean teeth. The longitudinal vibration of the scaling tip may be provided by d.c. pulse as a.c. excitation of a magnetostrictive stack. These tips provide an effective means for cleaning teeth. They do not have certain problems and shortcomings.

The cooling water nozzle is movable and hence it can inadvertently contact the scaling tip causing the water nozzle to vibrate. The water nozzle has an arcuate configuration such that when in use a portion of the water nozzle tends to contact the mouth tissue of the patient while the point of the scaling tip is positioned on the tooth itself. If the nozzle contacts the tip, the ultrasonic vibration of the tip is transmitted to the patient's tissue through the nozzle and can cause tissue burn through transmission of the ultrasonic energy directly to the tissue involved.

Furthermore, the end opening of the water nozzle is positioned immediately adjacent to the curved surface of the tip so that the water can flow over the tip directly onto the tooth surface being worked so that appropriate cooling and removal of dirt and scale will be effected. The flexible water nozzle may at times contact the tip and the ultrasonic vibrations of the tip against the water nozzle can cause a groove to be cut by the contact point of the end of water nozzle into the surface of the tip so that the tip is weakened and is caused to break off.

The flexible nature of the very small diameter water nozzle which permits adjustment of the water nozzle by the operator also results in the water nozzle at times moving from its proper position immediately adjacent to the scaling tip so that the water does not flow properly over the scaling tip. For this reason and in order to avoid contact between the water nozzle and the scaling tip, the user must manually adjust the water nozzle. This adjustment at times causes the nozzle to be bent and as it is bent and as it is bent back into position a kink occurs in the nozzle which makes it increasingly difficult to properly position and use the water nozzle.

In addition, the positioning of the water nozzle, particularly where there is a kink in it, tends to cause the water nozzle to contact the shield around the scaling tip. When this occurs concurrently with the water nozzle being in contact with the scaling tip, ultrasonic vibrations are transmitted to the shield and ultimately to the hand of the user of the dental cleaning device thereby causing the device to become uncomfortably hot and indeed even causing tissue burn if the user does not simply stop using the device or readjust the nozzle. In addition, this contact between tip, nozzle and shield generates a harsh, distracting, highly undesirable noise.

Accordingly, it is an object of this invention to provide an ultrasonic cleaning and scaling device in which the improper transmission of ultrasonic energy to the water tube and to the shield is avoided.

It is a further purpose of this invention to provide such a device as minimizes the problem of the improper positioning of the water tube and the improper contact between the water tube and the scaling tip as well as improper contact between the water tube and the shield.

As a consequence of obtaining these structural objectives, it is a more functional objective of this invention to prevent patient and user tissue burn, to prevent undesirable noise and to extend the life of the equipment involved.

A further object of this invention is to provide all of the above structural and functional objects in a mechanism in which can be employed not only with newly manufactured ultrasonic dental devices but also can be used as a retrofit on devices in the field so that these objectives can be obtained without having to replace all of the large number of such devices that are presently being used.

A further object of this invention is to provide these advantages by a mechanism which is inexpensive so that it will be adopted in this field and by a mechanism which does not increase the maintenance required for the scaling instrument and thus does not increase the down time factor. It is important that these problems be solved by a mechanism which neither introduces other problems nor requires greater skill and care than is now required to maintain the water nozzle properly positioned and properly aligned.

BRIEF DESCRIPTION

In one embodiment of the invention, a specially developed stabilizer element is provided. The ultrasonic devices are of a type well-known to the art. The devices are a hand piece in which a water nozzle and a scaling tip are in close proximity to one another. Both the water nozzle and the scaling tip are positioned adjacent to a grooved shield which is part of the insert in the hand piece. The tip vibrates longitudinally at a frequency above the frequency of the audible sound.

The stabilizer is a wafer like element with both a main opening and a minor opening. The main opening fits around the shield. The minor opening fits around the water nozzle. A groove engaging tab is shaped and dimensioned to fit into the upper groove on the shield. The stabilizer fits onto the shield with a slip fit.

It is contemplated that the minor opening by holding the water nozzle, in conjunction with the shield groove receiving tab and the major opening by holding the shaft will properly position the water nozzle to prevent undesired movement. In this manner the stabilizer will avoid the problems of prior art devices.

DESCRIPTION OF THE PREFERRED EMBODIMENTS

Figure 1:
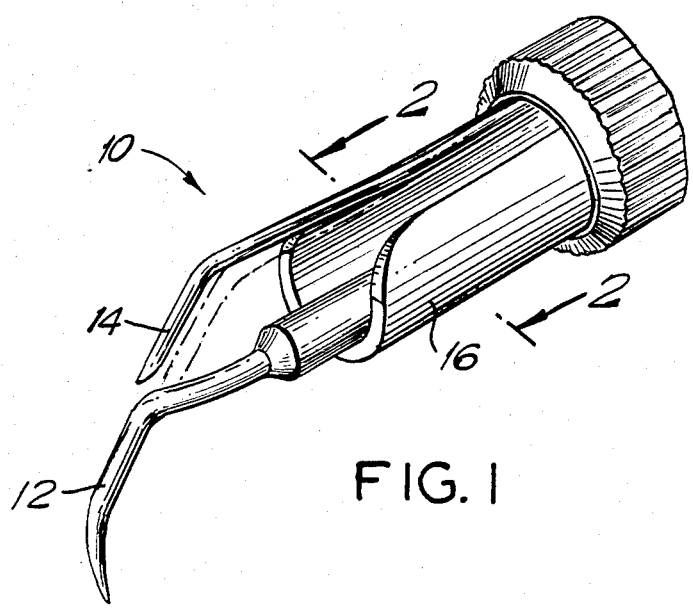
FIG. 1 is a perspective view of a prior art ultrasonic scaling device.

Referring now to the drawing and more particularly to FIG. 1, the reference numeral 10 denotes an ultrasonic dental cleaning and scaling insert. This insert 10 is inserted into handle (not shown) to provide the hand piece or cleaning tool. The insert 10 includes a scaling tip 12 in close proximity to a water nozzle 14. Water nozzle 14 is a metal tube about one mm in diameter and readily moves and bends. In FIG. 1, nozzle 14 is not in its proper position which is directly centered above and aligned with the scaling tip 12.

The insert 10 has a shield 16 attached to it. The shield has an elongated groove 18 along its top. The scaling tip 12 is positioned in the bottom part of shield 16 and the water nozzle 14 is positioned near the upper part of the shield 16.

Figure 2:
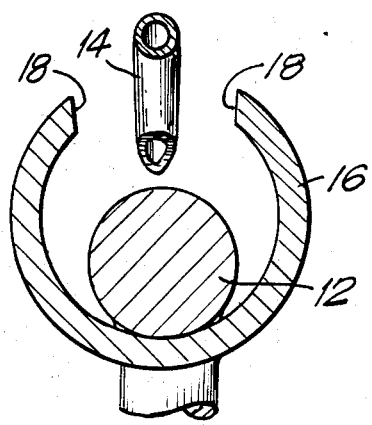
FIG. 2 is a sectional view through the shield of the tip taken substantially along the line 2—2 of FIG. 1.

As best shown in FIG. 2 the scaling tip 12 and water nozzle 14 are positioned very close to one another and near to the shield 16. The tool having the insert 10 is shown in FIGS. 1 and 2 is prone to the aforementioned problems.

Figure 5:
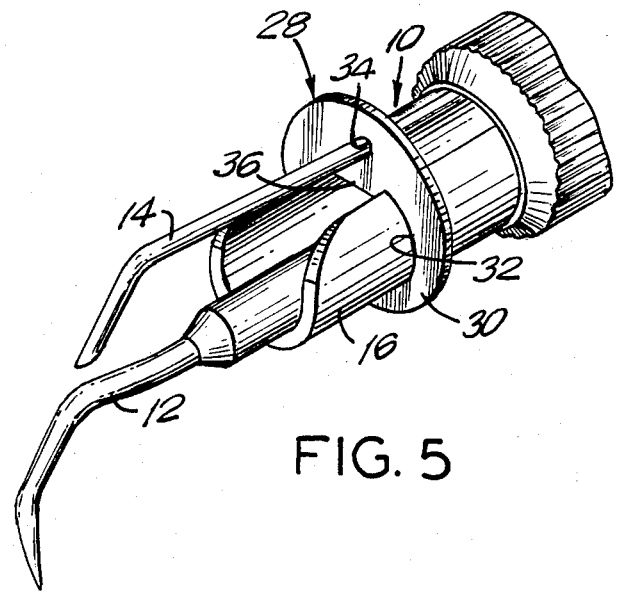
FIG. 5 is a view substantially analagous to FIG. 1 but showing the stabilizer of the present invention in place on the FIG. 1 device.

The reference numeral 28 denotes the stabilizer of the present invention which, as best shown in FIG. 5, fits onto the insert 10 to prevent undesired movement of the water nozzle 14.

The stabilizer 28 has a body portion 30. Formed in body portion 30 are a major opening 32 which fits around the shield 16 and a minor opening 34 which receives the water nozzle 14. The shield receiving opening 32 is shaped and dimensioned to receive, with a slip fit, the shield 16. The water nozzle receiving opening 34 is shaped and dimensioned to receive, with a slip fit, the water nozzle 14.

A groove engaging tab 36 extends into the major opening 32. The tab 36 is shaped and dimensioned to fit within the groove 18 of shield 16. Together groove engaging arm 36, shield receiving means 32 and water nozzle receiving means 34 prevent undesired movement of water nozzle 14 and holds it in proper position.

Figure 3:
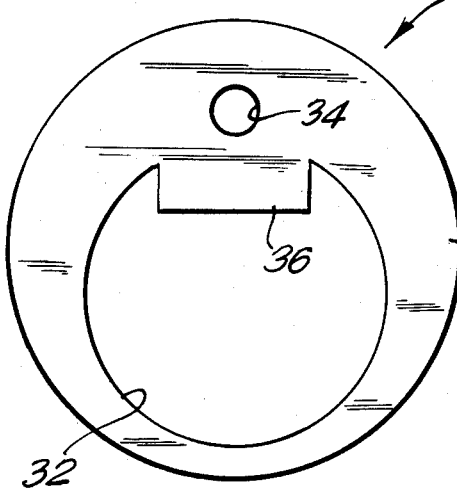
FIG. 3 is a plan view of the stabilizer of the present invention.
Figure 4:
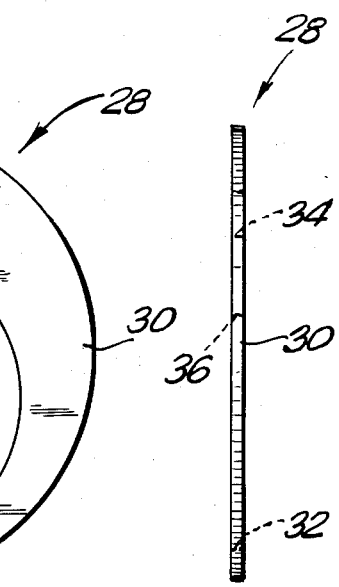
FIG. 4 is an end view of the stabilizer of the present invention.

As best shown in FIG. 3, in a preferred embodiment, the body 30 is generally circularly shaped in cross-section. The water nozzle receiving means in this embodiment is a small aperture formed in body 30 while the shaft receiving means is a large aperture formed in the body. As shown in FIG. 3, there are certain preferred, although not mandatory, dimensions for the various components of stabilizer 28.

Preferably, stabilizer 28 is constituted of a nylon material such as Delrin and is clear or white in color.

In use, the stabilizer 28 is mounted on the insert 10 such that the water nozzle 14 is inserted through water nozzle opening 34, the shield is inserted through shield opening 32 and the groove 18 slips over the tab 36. Thus, in place stabilizer 28 holds the water nozzle 14 in its proper position, as shown in FIG. 5, centered above and aligned with scaling tip 12. In this manner the stabilizer 28 achieves the objective recited above.

What I claim is:

1. A stabilizer improvement for use with an ultrasonic dental device of the type having a water nozzle and a scaling tip positioned adjacent to one another and having a shield around the tip, the shield having a longitudinal groove within which the water tube extends, the stabilizer improvement comprising:

a wafer-like body portion having a major first opening adapted to receive the shield and a minor second opening adapted to receive the shield and a minor second opening adapted to receive the water nozzle, said body portion including a tab extending into said first opening, said tab being dimensioned and positioned to extend into the groove of the shield when said stabilizer is mounted on the shield, whereby, when said stabilizer is mounted with said shield extending through said first opening, said water tube extending through said second opening and said tab extending into the groove of said shield, the water tube is positioned at a predetermined location to avoid contact with both the edges of the shield and the scaling tip as well as to be positioned adjacent to and directly over the scaling tip.

2. The stabilizer improvement of claim 1 wherein said second opening is positioned adjacent to said tab.

3. The stabilizer improvement of claim 1 wherein said first opening is dimensioned to provide a slip fit relationship with the shield and said second opening is dimensioned to provide a slip fit relationship with the water tube.

4. The stabilizer improvement of claim 3 wherein said second opening is adjacent to said tab.

* * * * *